(12) United States Patent
Feng et al.

(10) Patent No.: US 8,920,748 B2
(45) Date of Patent: Dec. 30, 2014

(54) BIOCHIP WITH A PIEZOELECTRIC ELEMENT FOR ULTRASONIC STANDING WAVE GENERATION

(75) Inventors: Guo-Hua Feng, Minhsiung Township (TW); Lai-Kwan Chau, Minhsiung Township (TW); Shu-Xiang Yang, Minhsiung Township (TW)

(73) Assignee: National Chung Cheng University, Minhsiung Township (TW)

( * ) Notice: Subject to any disclaimer, the term of this patent is extended or adjusted under 35 U.S.C. 154(b) by 457 days.

(21) Appl. No.: 13/098,622

(22) Filed: May 2, 2011

(65) Prior Publication Data

US 2012/0282140 A1    Nov. 8, 2012

(51) Int. Cl.
| | |
|---|---|
| *C12Q 1/68* | (2006.01) |
| *B06B 1/00* | (2006.01) |
| *G01N 21/75* | (2006.01) |
| *B01L 3/00* | (2006.01) |
| *G01N 21/17* | (2006.01) |
| *G01N 33/48* | (2006.01) |
| *G01N 21/55* | (2014.01) |

(52) U.S. Cl.
CPC ............... *G01N 21/17* (2013.01); *G01N 33/48* (2013.01); *G01N 21/553* (2013.01)
USPC ............. 422/417; 422/50; 422/128; 422/401; 422/408; 422/414; 422/500; 422/501; 422/502; 422/503

(58) Field of Classification Search
CPC ....... B82Y 15/00; G01N 1/286; G01N 1/405; G01N 21/17; G01N 21/553; G01N 33/48
USPC .................. 422/50, 128, 401, 408, 414, 417, 422/500–503
See application file for complete search history.

(56) References Cited

U.S. PATENT DOCUMENTS 7,869,013 B2 *   1/2011  Wang et al. ............... 356/73
2011/0142091 A1 * 6/2011  Wardle et al. ............. 374/45

FOREIGN PATENT DOCUMENTS

WO    WO2011061708    5/2011

OTHER PUBLICATIONS

Editor F. Chollet, "SU-8: Thick Photo-Resist for MEMS", MEMScyclopedia, Mar. 2, 2013, <http://memscyclopedia.org/su8.html>.

* cited by examiner

*Primary Examiner* — Dean Kwak
(74) *Attorney, Agent, or Firm* — Fishman & Associates, LLC.

(57) ABSTRACT

The present invention relates to a biochip with a piezoelectric element for ultrasonic standing wave generation. The biochip comprises an upper module, a lower module, and a chemical sensor. The piezoelectric element is integrated within the upper module of the biochip. The piezoelectric element can generate ultrasonic standing waves (USW) in the reaction chamber of the biochip by manipulating the operation frequency so the particles being detected can effectively move toward the QCM sensing surface. Hence, the biochip significantly increases the sensitivity and reduces the time required to reach equilibrium when undergoing USW excitation. The biochip of the present invention can be broadly applied to the bio-detection in medical and pharmaceutical fields.

16 Claims, 10 Drawing Sheets

BIOCHIP WITH A PIEZOELECTRIC ELEMENT FOR ULTRASONIC STANDING WAVE GENERATION

FIELD OF THE INVENTION

The present invention is related to a biochip, and more particularly to a biochip having a piezoelectric element that can improve the sensitivity of detection.

BACKGROUND OF THE INVENTION

Acoustic radiation forces generated by ultrasonic standing waves (USW) have useful applications in microfluidics. For example, acoustic radiation force can drive suspended particles toward and concentrate them to a specific position. It is a useful application that can be used in separation, washing or classification of particles and biological cells. Also, USW can increase the antibody-antigen encounter rate.

The radiation force on a spherical object, F, can be derived from the potential function, U, as shown in formula (1) below:

$$F = -\nabla U = -\nabla \left( V \left( f_1 E_{pot} - \frac{3}{2} f_2 E_{kin} \right) \right), \quad (1)$$

where V is the volume of a sphere with radius r. The parameters $f_1$ and $f_2$ are dimensionless correction factors which consider the compressibility of the object. $E_{pot}$ and $E_{kin}$ are the time-averaged potential and kinetic energy densities, given by formulas (2)-(5) below:

$$f_1 = 1 - \frac{\rho_0 c_0^2}{\rho c^2}, \quad (2)$$

$$f_2 = \frac{2(\rho - \rho_0)}{2\rho + \rho_0}, \quad (3)$$

$$E_{pot} = \frac{\langle p^2 \rangle}{2\rho_0 c_0^2}, \quad (4)$$

$$E_{kin} = \frac{\rho_0 \langle v^2 \rangle}{2} \quad (5)$$

where $\rho$ and c are the density and the sound velocity of the sphere. $\rho_0$ and $c_0$ are the density and the sound velocity of the medium. $p^2$ and $v^2$ are the mean-square fluctuation of the incident pressure and velocity of the acoustic field at the particle's location. If the particle is rigid, $f_1=f_2=1$. Formula (1) is valid under the conditions that the radius of the sphere is much smaller than the acoustic wavelength $\lambda$, of the medium and is much larger than the medium volume element displacement amplitude. If considering only one-dimensional force and a harmonic sound source, the acoustic radiation force can be obtained from formula (6) below:

$$F = -\frac{\partial}{\partial z} U(z) = \frac{\pi}{2\rho_0 c_0^2} \left( f_1 + \frac{3}{2} f_2 \right) V p_0^2 v \sin\left( 2\pi \frac{z}{\lambda/2} \right). \quad (6)$$

The force is proportional to the particle volume and the sound wave intensity and is related to the wavelength of the acoustic wave.

On the other hand, quartz crystal microbalance (QCM) based bio-sensing technology has been applied successfully to investigate molecular interactions over the past few years. This technique is useful for detecting both gases and liquids and has proven to be a versatile label-free method. The deficiency of QCM is while operating in a liquid medium, the sensitivity of QCM will be affected by the viscosity and density of the contacting liquid. These effects reduce sensitivity due to liquid damping.

In order to expand the applications of biochips based on QCM, integrating QCM and biochip for enhanced QSW-based biochip detection sensitivity and reduced detection time is necessary.

SUMMARY OF THE INVENTION

To avoid the negative effects of liquid medium, the present invention is to provide a biochip with a piezoelectric transducer for ultrasonic standing wave generation, which can improve the sensitivity of detection and reduce the time of detection.

The present invention provides a biochip with a piezoelectric element for ultrasonic standing wave generation, comprising an upper module, a lower module and a chemical sensor.

The upper module has a carrier, a photoresist layer, a flow inlet, a flow outlet, an opening of a reaction chamber, a piezoelectric element, an O-ring and multiple spacers, and said photoresist layer is formed on one side of the surface of said carrier. The flow inlet, the flow outlet and the opening of a reaction chamber are formed through the photoresist layer and the carrier; the piezoelectric element is set on the surface of the photoresist layer; the O-ring is set on the other surface of said carrier surrounding the opening of a reaction chamber and the spacers are set on the other surface of the carrier near the edges of the carrier.

The lower module has a carrier, an O-ring and multiple spacers. The carrier, the O-ring and the spacers of the lower module are set corresponding to the carrier, the O-ring and the spacers of the upper module, respectively.

The chemical sensor is mounted between the O-ring of the lower module and the O-ring of the upper module. Attaching the upper module and the lower module makes the chemical sensor to enclose the opening of a reaction chamber to form the reaction chamber.

The chemical sensor is a quartz crystal microbalance sensor, a surface plasmon resonance sensor or a particle plasmon resonance sensor.

According to the present invention, the principle of the surface plasmon resonance sensor is using the plasmon on the surface for detection. The plasmon on the surface is formed by electromagnetic waves along an interface between metal and dielectric. Polarized incident light parallel to the surface at a resonance angle results in attenuated total reflection, because the polarized light is coupled to the plasmon on the surface, and the energy of the polarized light will be absorbed. In this aspect, because of the resonance of the plasmon on the surface, the reflection of the polarized light will be decreased. Due to resonance of the plasmon on the surface, the index of refraction of the polarized light is very sensitive to the dielectric on the metal surface. The plasmons on the surface have different resonance angles when the refractive index of the dielectric changes. With the same dielectric, the strength of resonance of the plasmon on the surface will depend on the thickness of the dielectric. Based on this principle, the surface plasmon resonance sensor with immobilized specific receptor on the metal surface can detect the binding process of analyte and the immobilized receptor at the interface. During the process, the local index of refraction of the layer adjacent to the metal surface changes, and the surface plasmon resonance sensor will detect the change of the index of refraction.

According to the present invention, the particle plasmon resonance sensor is also called the localized surface resonance sensor. The principle of detection of the particle plasmon resonance sensor is while an incident light is resonant with the precious metal nanoparticles of the particle plasmon resonance sensor, the nanoparticles display an extinction band, and the extinction band is related to the index of refraction of the medium. Functionalized nanoparticles can act as chromophores. After interaction with an analyte, the extinction band of the functionalized nanoparticles will change. Thus, by selecting an appropriate receptor on the surface of the nanoparticles, even the analyte that cannot be detected by UV-vis spectrometer can be detected by the particle plasmon resonance sensor.

According to the present invention, the carrier is, for example, a glass slide, a steel sheet or a silicon wafer.

According to the present invention, the piezoelectric element preferably generates ultrasonic standing waves with a frequency from 100 kHz to 2 MHz.

According to the present invention, the distance between said piezoelectric element and said chemical sensor ranges from 0.2 mm to 4 mm, and preferably, 2 mm.

The biochip of the present invention significantly increases the sensitivity and reduces the time required to reach equilibrium with USW excitation. Hence, the biochip can be broadly applied to the bio-detection in medical and pharmaceutical fields.

DETAILED DESCRIPTION OF THE INVENTION

Device Fabrication
1. Construction of Biochip

Figure 1:
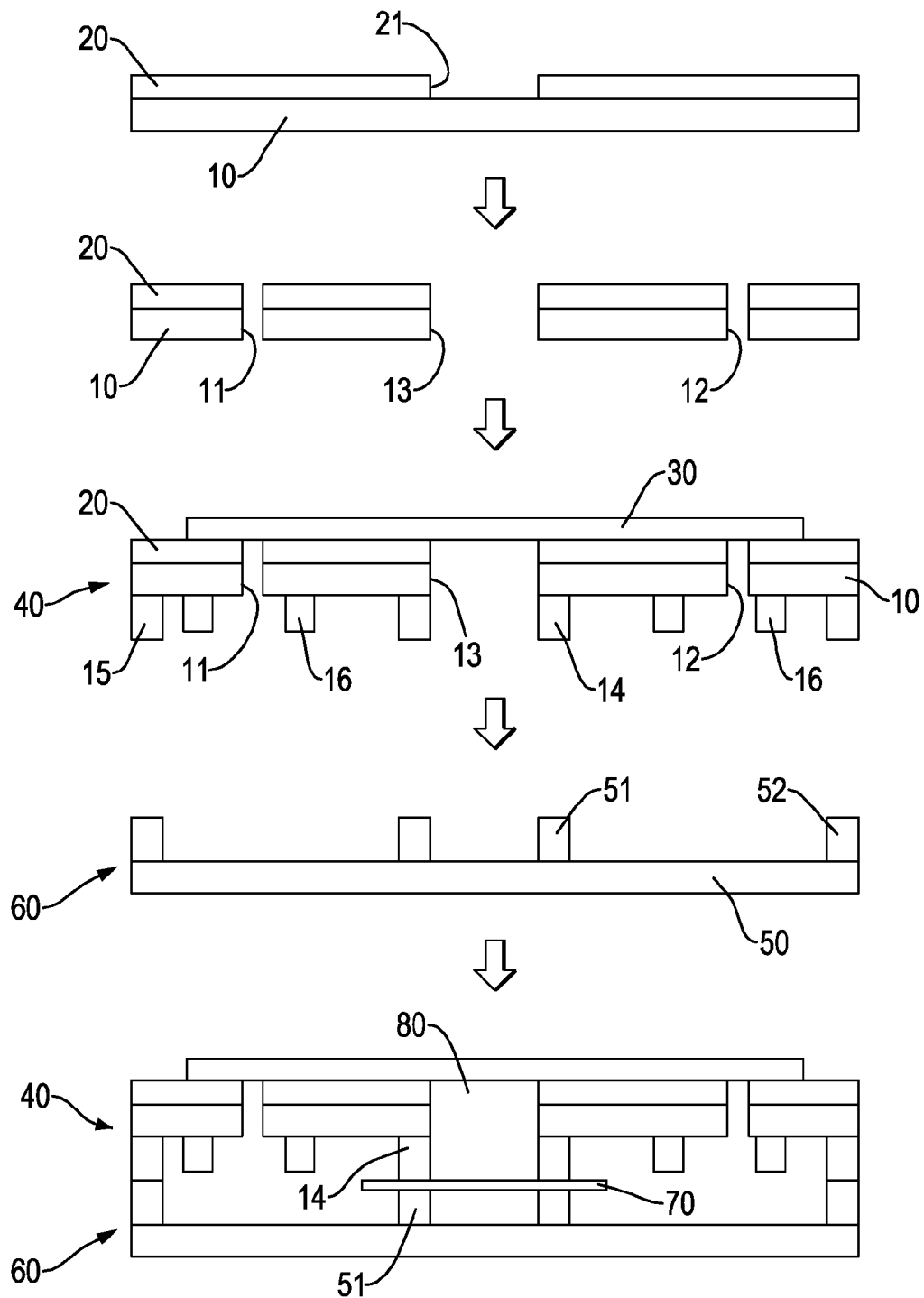
FIG. 1 shows the construction process of a biochip of the present invention.

With reference to FIG. 1, the steps of constructing a biochip are as follows.

(a) Preparing a glass slide (10), wherein the size of the glass slide is 25.4 mm.times.8 mm.times.1 mm, the glass slide has two corresponding surfaces, one of the surfaces is coated with an epoxy-based negative photoresist solution with a viscosity of 51500 cSt (also known as SU-8 100, produced by Microchem) to form a photoresist layer (20), and the thickness of the photoresist layer (20) is between 100 .mu.m and 2 mm. In the embodiment of the present invention the thickness of the photoresist layer (20) is 200 .mu.m. The surface of the photoresist layer (20) is patterned to define predetermined positions respectively corresponding to a flow inlet (11), a flow outlet (12), and an opening of a reaction chamber (13). Multiple micro channels (21) are formed according to the predetermined positions patterned on the photoresist layer (20).

(b) Based on the predetermined positions patterned on the photoresist layer (20), drilling through the glass slide (10) to form the flow inlet (11), the flow outlet (12) and the opening of a reaction chamber (13). The flow inlet (11), the flow outlet (12) and the opening of a reaction chamber (13) are connected by the micro channels (21).

(c) Attaching a piezoelectric element (30) (Sunny Tech Co., Taiwan) on the surface of the photoresist layer (20), wherein the size of the piezoelectric element (30) is 20 mm×8 mm×2 mm; and attaching an O-ring (14), two spacers (15) and two tubes (16) on the other surface of the glass slide (10) to form an upper module (40). The O-ring (14) and the spacers (15) are made by polydimethylsiloxane (PDMS), the inner diameter of the O-ring (14) is 6 mm, the outer diameter of the O-ring (14) is 8 mm and the thickness of the O-ring (14) is 1.5 mm. The spacers (15) are separately set on the surface of two corresponding edges of the glass slide (10) and the size of the spacers is 4 mm×8 mm×2 mm. The tubes (16) are separately set on the surface of the glass slide (10) surrounding the flow inlet (11) and the flow outlet (12) to allow fluid to pass through the tubes (16) to the flow inlet (11) and the flow outlet (12), and the diameter of the tubes is 2 mm.

(d) Preparing another glass slide (50), wherein the size of the glass slide (50) is equal to the glass slide (10); and attaching an O-ring (51) and two spacers (52) on the surface of the glass slide (50) corresponding to the O-ring (14) and the spacers (15) of the upper module (40) with pressure sensitive adhesive tape (9019 double-sided tape, 3M) to form a lower module (60). The size of the O-ring (51) of the lower module (60) can be bigger than the O-ring (14) of the upper module (40). In the embodiment of the present invention the inner diameter of the O-ring (51) is 8 mm and the outer diameter of the O-ring (51) is 10 mm. The size of the spacers (52) is equal to the size of the spacers (15) of the upper module (40).

(e) Preparing a chemical sensor (70), and in the embodiment of the present invention the chemical sensor (70) is a QCM sensor. And the chemical sensor (70) placing between the O-ring (51) of the lower module (60) and the O-ring (14) of the upper module (40). And then combining the upper module (40) and the lower module (60) to make the O-ring (14) of the upper module (40) compressed on the chemical sensor (70) to enclose the opening of a reaction chamber (13) to form the reaction chamber (80). The biochip construction is completed.

2. Operating Principle of Biochip

Figure 2A:
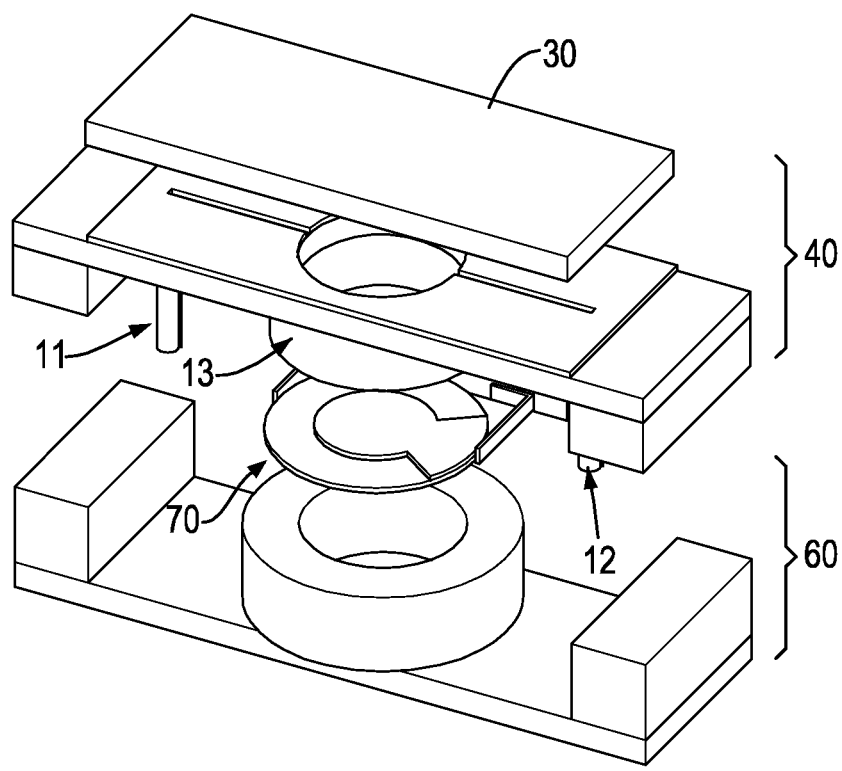
FIG. 2 shows the three-dimensional exploded view of a biochip of the present invention.

With reference to FIG. 2A, the biochip comprises the upper module (40), the lower module (60) and the chemical sensor (70). During operation, fluid is injected into the flow inlet (11) through the micro channels (21) to the reaction chamber (80). The fluid contains multiple bio-particles. The surface of the chemical sensor (70) is coated with gold electrodes and then a recognition molecule targeting to an analyte is immobilized on surfaces of the gold electrodes. The bio-particles in the fluid will react with the recognition molecule on the surface of the chemical sensor (70). The frequency of USW generated by the piezoelectric element (30) is adjusted depending on the quantity of the bio-particles in the fluid.

Figure 2B:
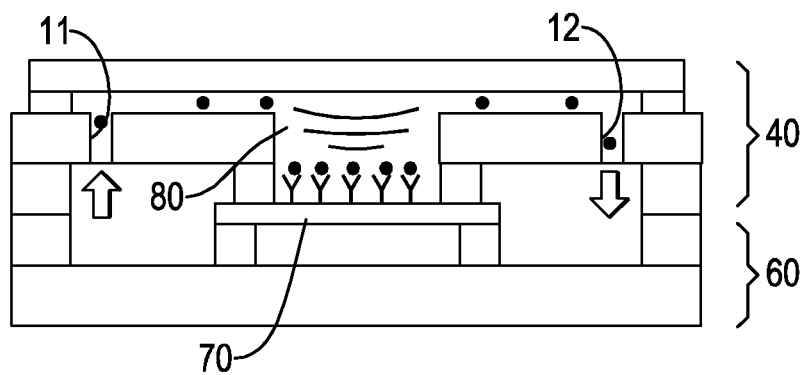

The sensitivity of the biochip is improved by USW. As shown in FIG. 2B, the bio-particles are driven toward the sensing surface of the QCM sensor of the biochip with USW excitation.

Experimental Materials
Equipment:
QCM sensor (Taitien Electronics Co., Taiwan), wherein the diameter is 8 mm and the thickness is 166 μm. The resonant frequency of the QCM sensor is 10 MHz, the QCM sensor comprises gold electrodes, and the diameter of the gold electrodes is 3.6 mm. Piezoelectric element (Sunnytec Co., Taiwan), wherein the diameter is 2 cm and the thickness is 800 μm. Latex particles (Invitrogen Company, USA), wherein the size of the latex particle is 10 μm. The thermocouple (Center Technology Corp., Taiwan), Model #304.

Chemical Reagent:
cystamine dihydrochloride (Sigma, USA). 4-(2-hydroxyethyl)-1-piperazineethanesulfonic acid, HEPES (Sigma, USA). 1-ethyl-3(3-dimethylaminopropyl)-carbodiimide hydrochloride, EDC (Sigma, USA). N-hydroxysuccinimide, NHS (Sigma, USA) biotin (Sigma, USA). streptavidin (Sigma, USA). Phosphate buffered saline, PBS, which is prepared by 8 mM $Na_2HPO_4$ and 1.4 mM $kH_2PO_4$. All aqueous solutions are prepared with water purified by a Ropure ST water purification system (Barnstead, USA) with a specific resistance of 18 MΩ cm.

Experimental Method
A reagent is injected into the biochip using a flow rate controllable syringe pump (KDs Co., USA, Model no. 780101). The reagent is streptavidin solution. The effects of different flow rate injection to the reaction chamber and the long-term stability of the quiescent liquid in the reaction chamber are investigated. Frequency monitoring is performed by connecting the QCM sensor to a homemade circuit board and sending the resulting signal to a frequency counter (Aligent Co., Model no. 53131A). The readout data of the frequency counter is simultaneously acquired to a computer through the RS232 port.

To generate USW inside the reaction chamber of the biochip, the piezoelectric element is actuated with specific frequency and amplitude. A 100 mV peak-to-peak sinusoidal wave driving signal is produced by a function generator (Tetronix Co., Model: AFG3021), amplified by an RF power amplifier (Bell Co., Model 325LA) and delivered to the piezoelectric element at $25V_{pp}$. An appropriate frequency based on the 2 mm distance between the piezoelectric element and the QCM sensor is estimated by said formulas (2) and (6) to be 185 kHz.

To verify the estimated frequency as a functional value, a vertically inverted microscope (Olympus Co., model XI71) is used to monitor the motion of latex particles inside the reaction chamber of the biochip. To facilitate inspection of the effect of USW, the gold electrodes on the QCM sensor are chemically etched to be made transparent. While the latex particles mixed with purified water are injected into the reaction chamber, images are obtained by setting the microscope to focus around the region of the sensing surface of the QCM sensor. The obtained images show that large numbers of latex particles are observed near the QCM sensor when the frequency is 185 kHz. Few latex particles are observed when the frequency is significantly different than 185 kHz. Thus, 185 kHz is applied for USW generation in the following experiments.

Temperature measurement is performed with the thermocouple. The reaction chamber is filled with the purified water and a temperature sensor is placed inside the reaction chamber. The temperature sensor records temperature data after activating USW for different working periods. The purpose of the temperature measurement is to ensure that temperature effects resulting from USW will not degrade the activity of the bio-particles. The frequency shift of the QCM sensor and the temperature change in the reaction chamber are simultaneously monitored and compared to investigate the relation between the frequency shift and the temperature change.

To sum up, 0.02 M cystamine solution is injected into the biochip with a flow rate of 15 μl/min. The cystamine solution fills up the reaction chamber. The gold electrodes of the QCM sensor undergo in-situ modification by the cystamine solution, reaching a steady state at about half an hour. The purified water is then injected to rinse the reaction chamber and remove the non-immobilized bio-particles. Rinsing is repeated three times. Next, for immobilization of biotin on the surface of the QCM sensor being cystamine modified, 5 mM of biotin solution is injected into the reaction chamber. The biotin solution consists of 0.01M HEPES buffer, 0.1M EDC and 0.025M NHS, and the pH of the biotin solution is 7.4.

Follow the experiment method described above to prepare two biochips. For one biochip, no USW excitation is used. For the other biochip, 30 seconds of USW excitation is applied to concentrate biotin near the surface of the QCM sensor being cystamine modified to increase the amount of biotin binding. Preparation of each biochip is followed by three times of DI water rinsing.

Biochips with and without USW excitation are tested for streptavidin reactivity for various concentrations of streptavidin (from 1 μg/mL to 100 μg/mL) in PBS solution. Each test is monitored in real time by recording the frequency response of the QCM sensor (Kim et al., *Impedance characterization of a piezoelectric immunosensor Part I: Antibody coating and buffer solution*, Biosensor and Bioelectronics, 18 (2003) 83-89). Tests are performed in the biochips with USW-enhanced biotin immobilization under the following three conditions: (1) no USW excitation; (2) USW excitation of 15 sec; (3) USW excitation of 30 sec.

Results and Discussion
1. The Effects of Temperature
Long-term stability testing was performed after filling the reaction chamber of the biochip with the purified water, with no more liquid passing through. The result shows a frequency fluctuation within 3~5 Hz. If liquid is continuously injected into the biochip with different flow rates, the maximum frequency fluctuations within one hour are in the range of 3~5, 4~6, 7~12 and 10~20 Hz for flow rates of 10, 15, 20 and 25 μL/min, respectively, and the result of the frequency fluctuations caused by different flow rates is based on continuous 5-hour data monitoring.

Figure 3:
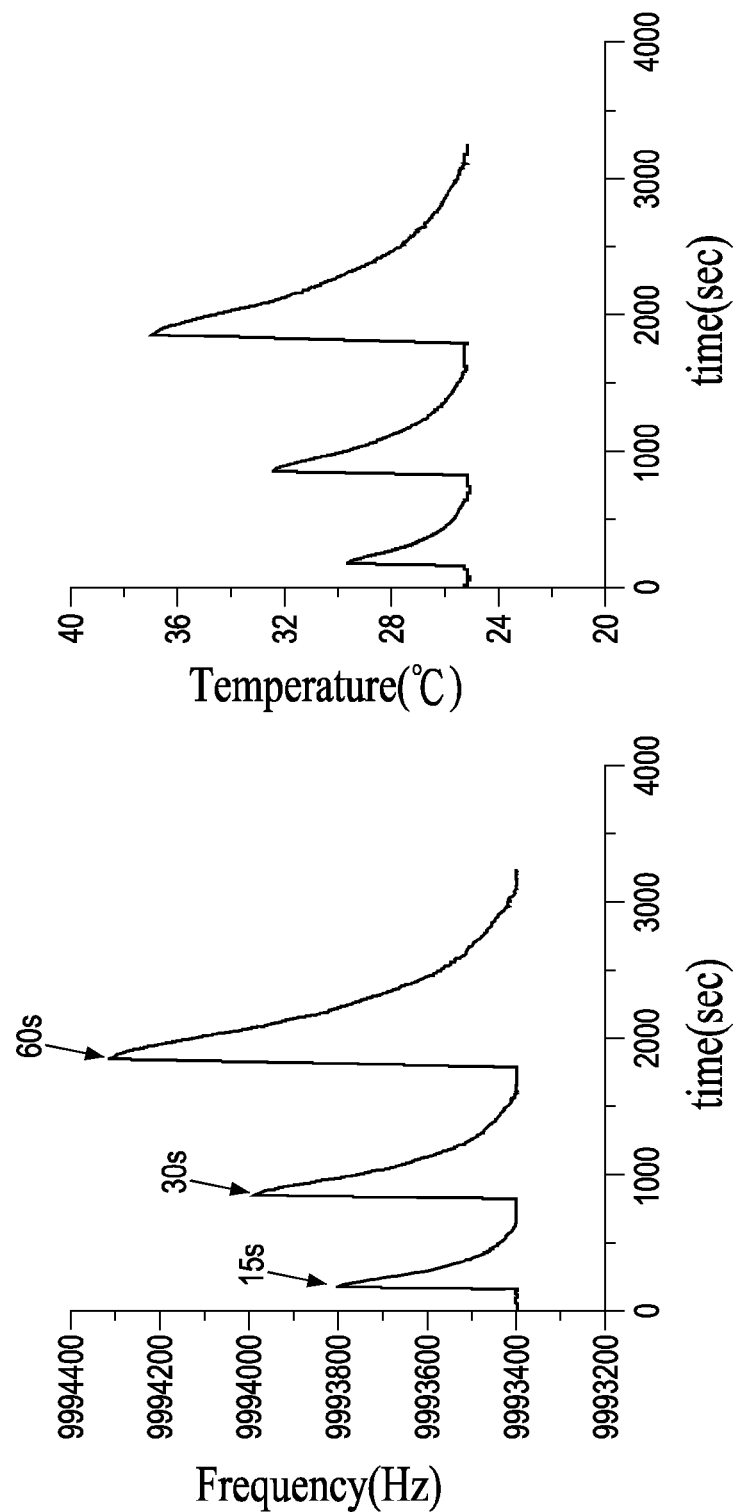
FIG. 3 shows the change of frequency and temperature of the biochip chamber with USW excitation at 185 kHz.

USW produced by the piezoelectric element causes the temperature inside the reaction chamber to rise and increases the frequency detected from the QCM sensor. As FIG. 3 shows, for USW excitation of 15, 30 and 60 seconds, the maximum temperature increases by 4.8, 7.6 and 12.5° C., respectively, relative to an initial temperature of 25.2° C. The corresponding frequency shifts are approximately 400, 600 and 900 Hz, respectively, relative to a base frequency of 9.9934 MHz.

Although the frequency is observed to shift during USW excitation, the frequency nevertheless returns to its baseline after a suitable cooling period. This result shows that USW excitation does not cause the baseline of the frequency to shift, which is an important factor for ensuring that the sensitivity enhancement of the biochip caused by USW excitation can be reliably employed for improved QSW biochips.

2. The Sensitivity of the Biochip without USW Excitation

Figure 4:
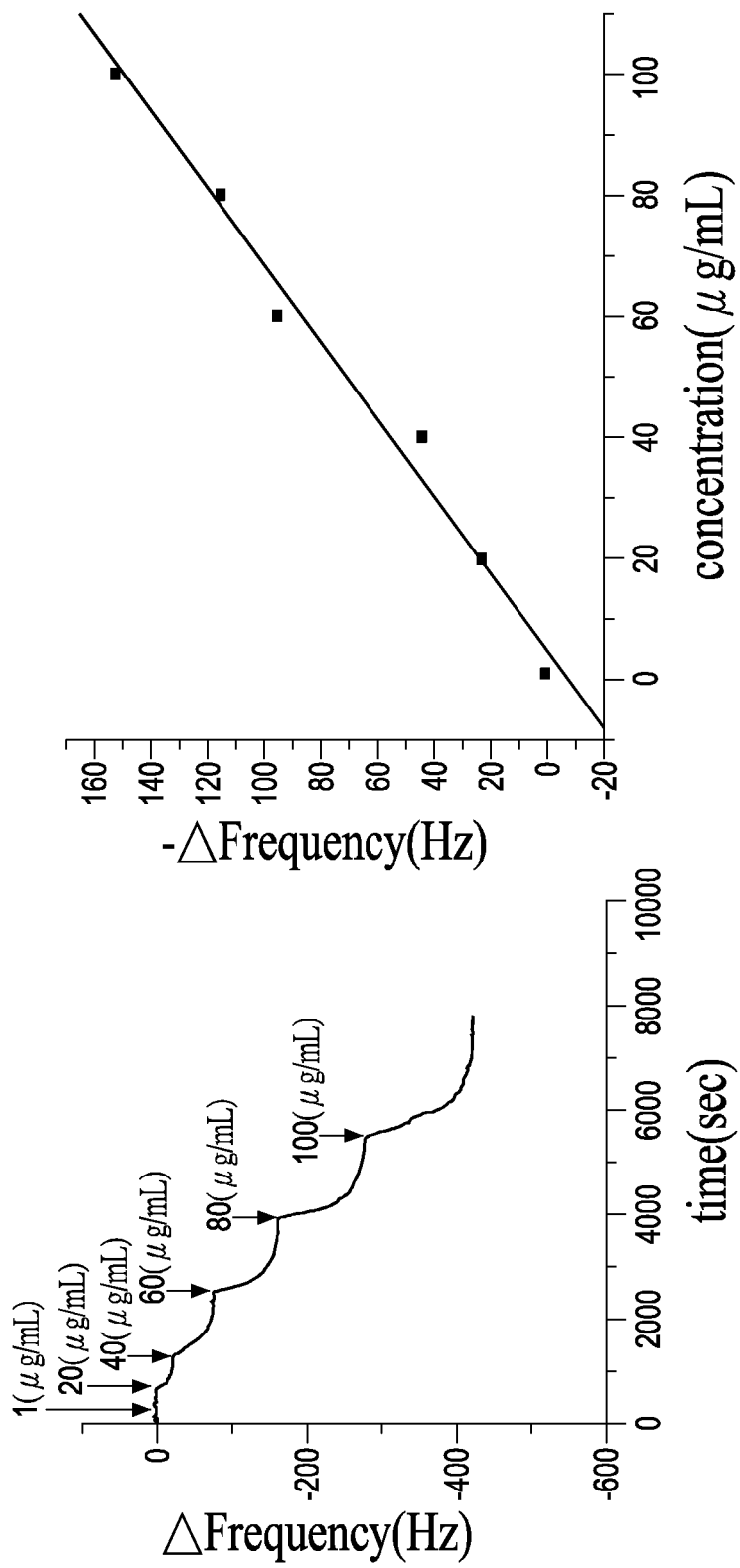
FIG. 4 shows the change of frequency of the biochip reacting with various concentrations of streptavidin without USW excitation.

FIG. 4 shows the sensitivity of the biochip without USW excitation, with various concentrations of streptavidin: 1, 20, 40, 60, 80 and 100 μg/mL. The lowest concentration responds within a noise level range, wherein the noise level range means a range of useless signal. When the concentration of streptavidin is 20 μg/mL, the frequency of the QCM sensor shifts for approximately 22 Hz. With increasing concentration, the frequency shifts are greater. When the concentration of streptavidin is 100 μg/mL, the frequency drop is 150 Hz. Similarly, the reaction time required to reach chemical equilibrium increases with increasing streptavidin concentration, starting at 400 sec at 20 μg/mL and reaching 1500 sec at 100 μg/mL. The relationship between the streptavidin concentration and the measured frequency shift shows a good linear correlation (R>0.992) with a slope/sensitivity of 1.57 Hz/(μg/mL) and the standard deviation is 7.89 Hz.

3. The Sensitivity of the Biochip with USW Excitation

Figure 5A:
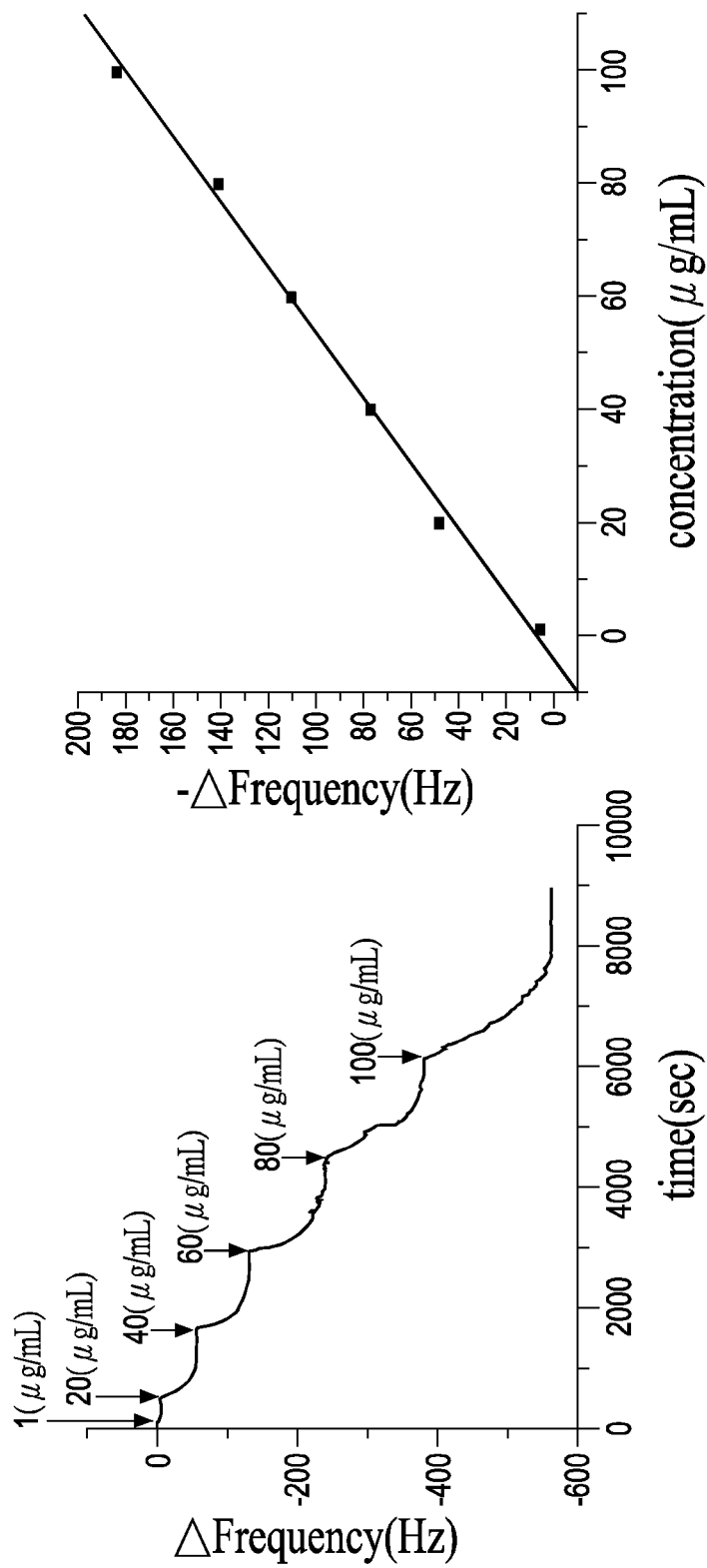
FIG. 5A shows the change of frequency of the biochip reacting with various concentrations of streptavidin with USW excitation just during biotin immobilization.
Figure 5B:
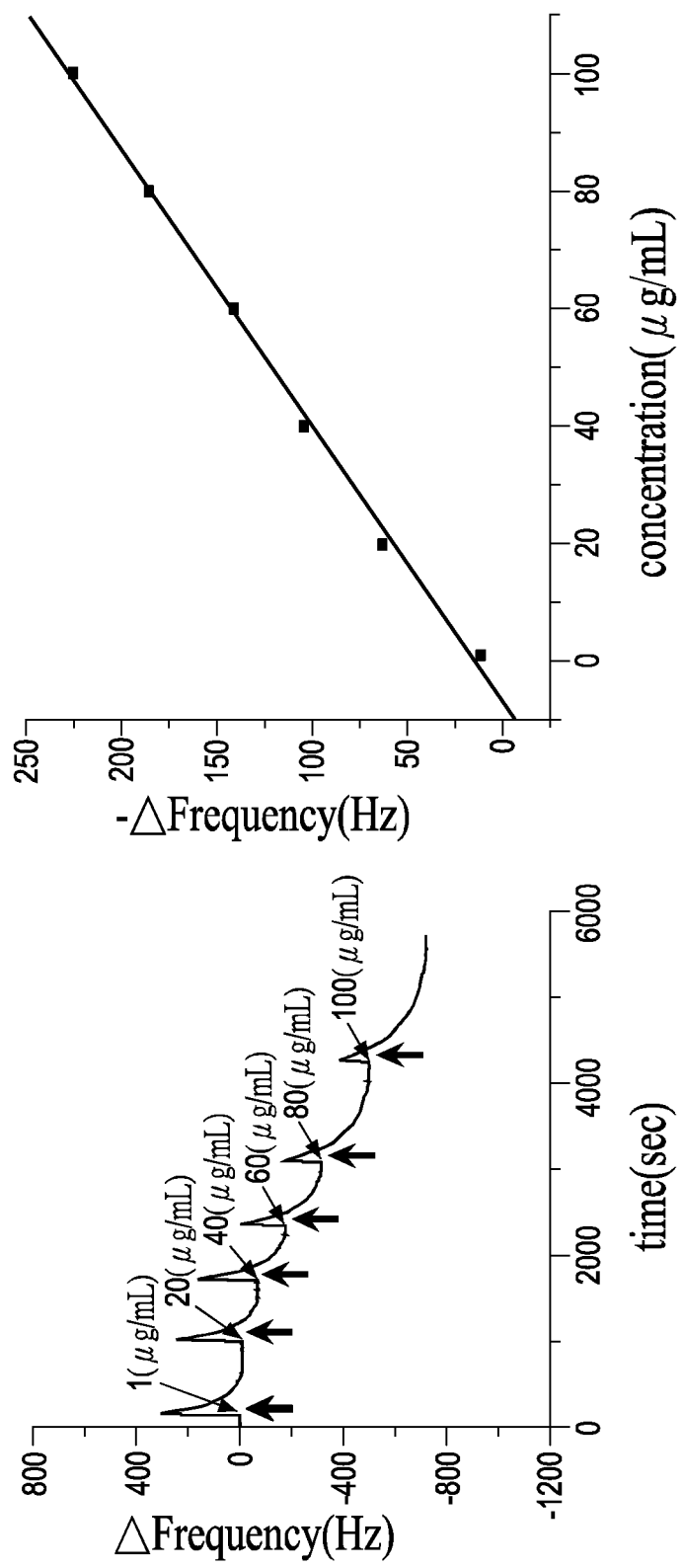
FIG. 5B shows the change of frequency of the biochip reacting with various concentrations of streptavidin with USW excitation for 15 sec.
Figure 5C:
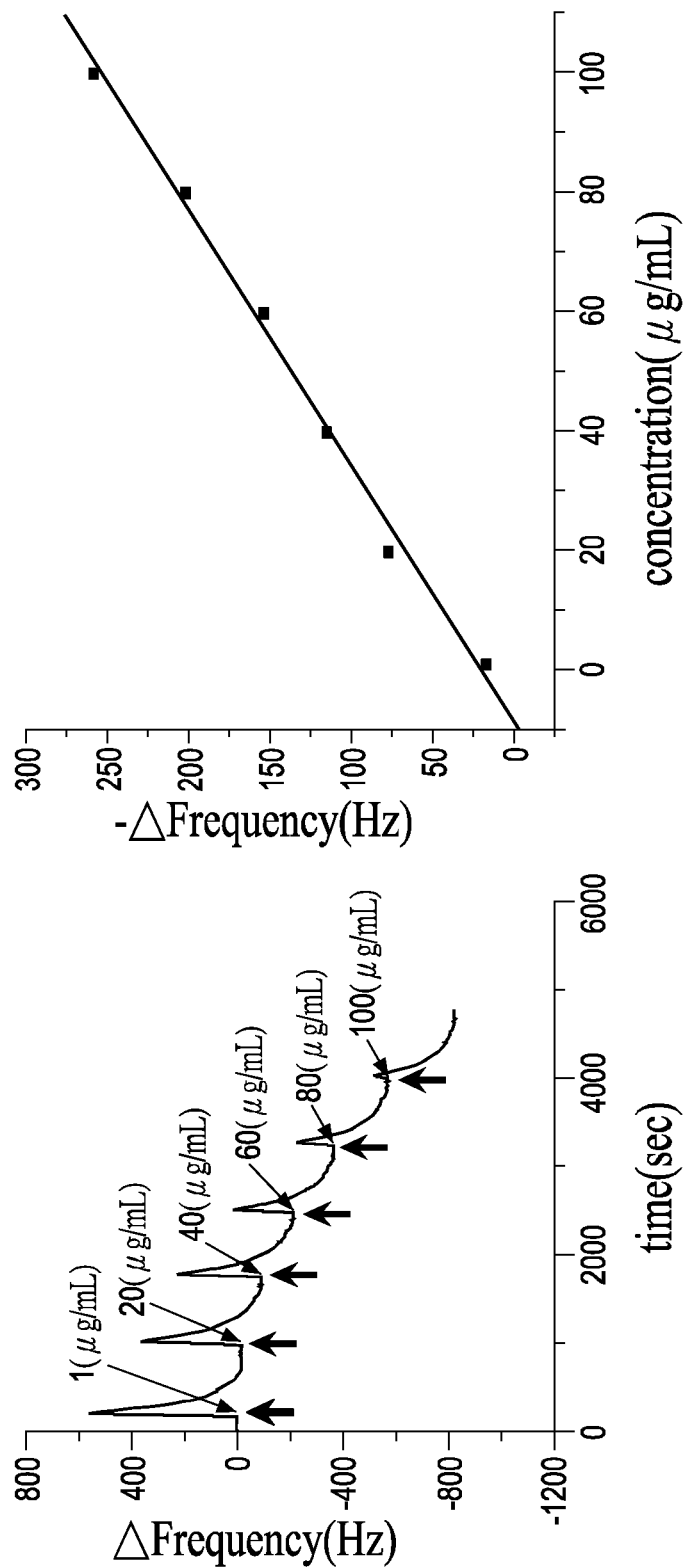
FIG. 5C shows the change of frequency of the biochip reacting with various concentrations of streptavidin with USW excitation for 30 sec.

FIGS. 5A-5C show the results of biochip detection with different levels of USW excitation. FIG. 5A shows the results for the biochip with USW excitation only during biotin immobilization while no USW excitation is applied when streptavidin of concentrations 1, 20, 40, 60, 80 and 100 μg/mL are injected. When the concentration of streptavidin is 1 μg/mL, the frequency of the biochip displays a distinguishable drop. Each of the various concentrations of streptavidin shows larger frequency drop than its analog in FIG. 4 without USW excitation. Required times to reach chemical equilibrium for the corresponding concentrations of streptavidin are 215, 470, 790, 1025, 1400, and 1665 sec, respectively. The results also reveal a good linear relation (R>0.997) with a slope/sensitivity of 1.73 Hz/(m/mL) and a standard deviation of 4.58 Hz.

As FIGS. 5B and 5C show, the USW excitation is employed not only during biotin immobilization but also during measurement for 15 sec and 30 sec respectively. The USW excitation begins just after injecting the streptavidin solution into the biochip and filling the reaction chamber. Both the responses via 15 and 30 sec excitations exhibit peaks, which gradually decrease to steady state, and this means the frequency drop of reaching equilibrium decreases. In FIG. 5B, the USW excitation for 15 sec shows frequency drops larger than that without USW excitation in FIG. 4. In FIG. 5C, the USW excitation for 30 sec shows frequency drops even greater than that by USW excitation for 15 sec. Both the results show a good linear relation between the frequency shift and streptavidin concentration, with correlation coefficients of 0.999 and 0.997, standard deviations of 4.78 and 7.46 Hz respectively for 15 sec and 30 sec USW excitation. With regard to the sensitivity of the biochip with USW excitation for 15 and 30 sec, the sensitivity of the biochip with USW excitation for 15 sec is 2.13 Hz/(μg/mL) and the sensitivity of the biochip with USW excitation for 30 sec is 2.33 Hz/(μg/mL), and the sensitivity of the biochip with USW excitation for 30 sec is a 48% increase compared to the sensitivity of the biochip without USW excitation.

Figure 6A:
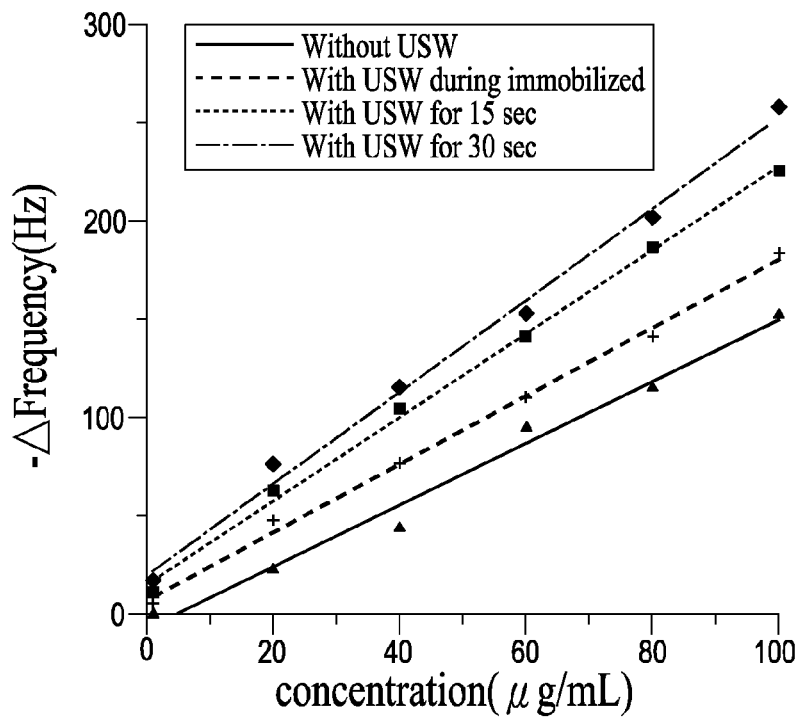
FIG. 6A shows the relationship of streptavidin concentration and frequency of the biochip with multiple USW excitations.
Figure 6B:
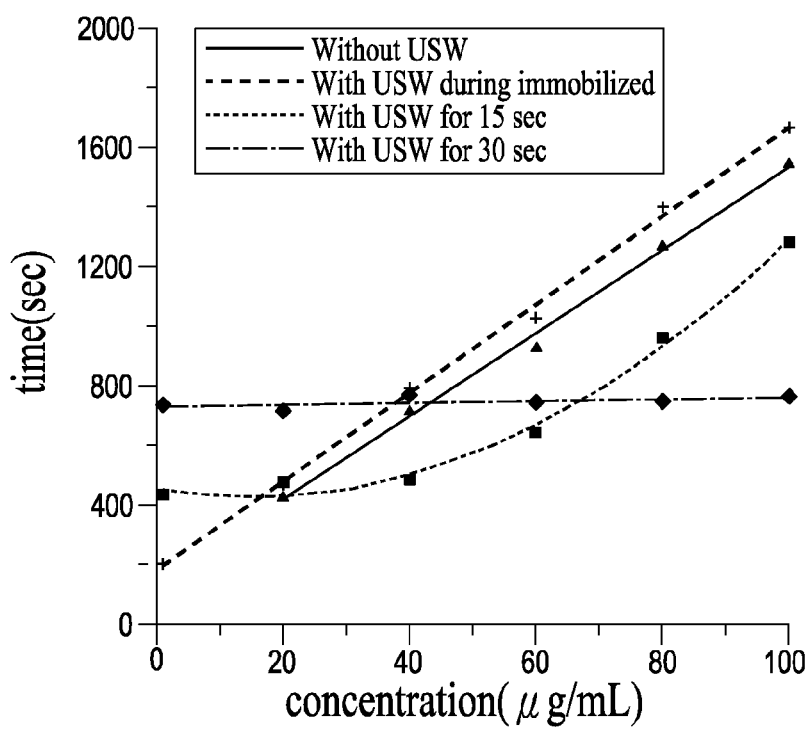
FIG. 6B shows the relationship of response time and streptavidin concentration of the biochip with multiple USW excitations.

Further, as FIG. 6 shows, the required time to reach chemical equilibrium is much reduced. For example, the biochip with USW excitation for 30 sec takes only 800 sec to reach chemical equilibrium while 100 μg/mL streptavidin is being injected, which is about half the time required for the biochip without USW excitation to reach the equilibrium.

4. Clarification of Effects of USW and Temperature on Sensor Responses

Figure 7A:
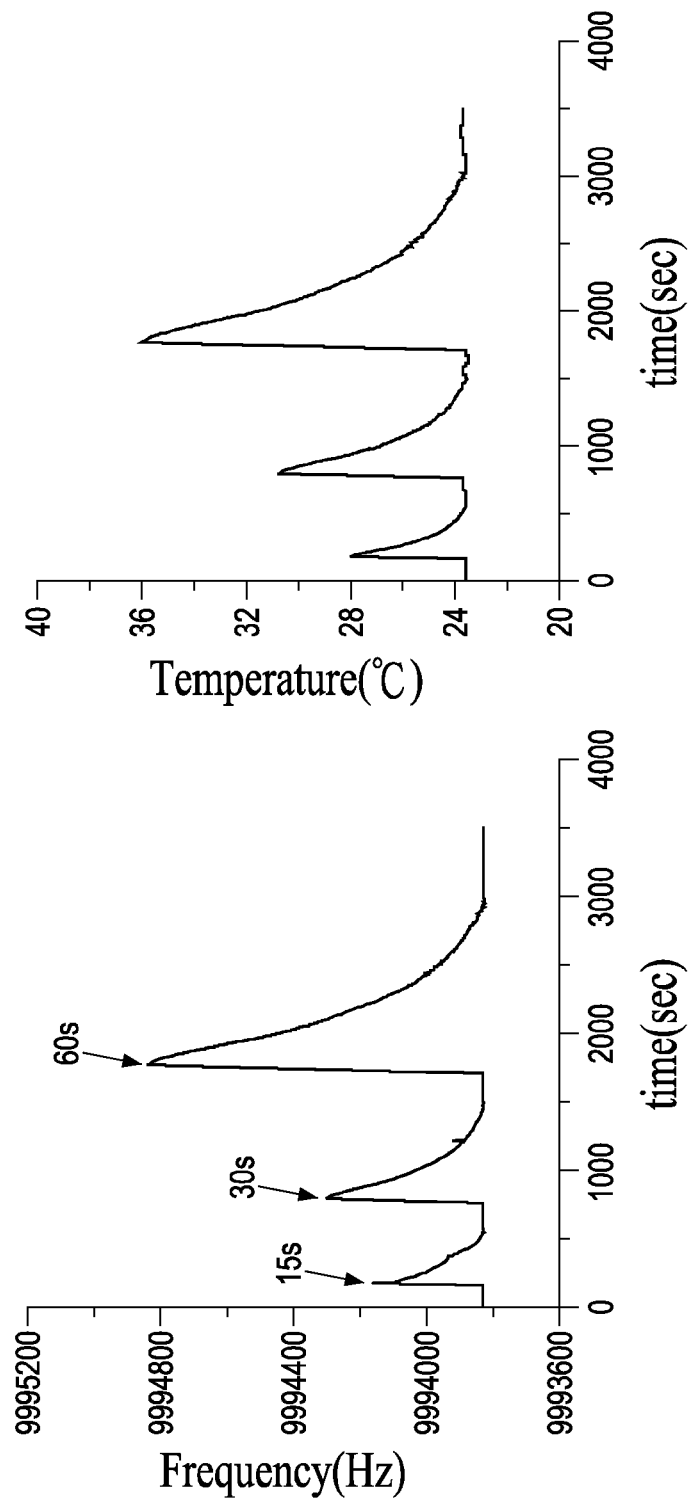
FIG. 7A shows the change of frequency and temperature of the biochip chamber with USW excitation at 300 kHz.

Confirming that the observed enhancement of the biochip said above is a result of USW excitation instead of a result of temperature rise during piezoelectric element actuation is important. The following scheme examines this issue. As FIG. 7A shows, the piezoelectric element is driven by a 300 kHz sinusoidal wave as the piezoelectric element actuation signal to provide a USW excitation with a frequency of 300 kHz, wherein a distance between the piezoelectric element and the QCM sensor is 2 mm and the rest experimental conditions are the same as the USW excitation with a frequency of 185 kHz, including that the amplitude from the function generator is set as 115 $mV_{pp}$ and then amplified to 25 $V_{pp}$ to drive the piezoelectric element. The result shows temperature rises are about 4.5, 7.2 and 12.2° C. from a base temperature of 23.8° C. for the USW excitation with a frequency of 300 kHz of 15, 30 and 60 sec, respectively. Compared to FIG. 3, the temperature rises are respectively about 4.8, 7.6 and 12.5° C. from the base temperature for the USW excitation with a frequency of 185 kHz. The rising of temperature is approximately the same.

Figure 7B:
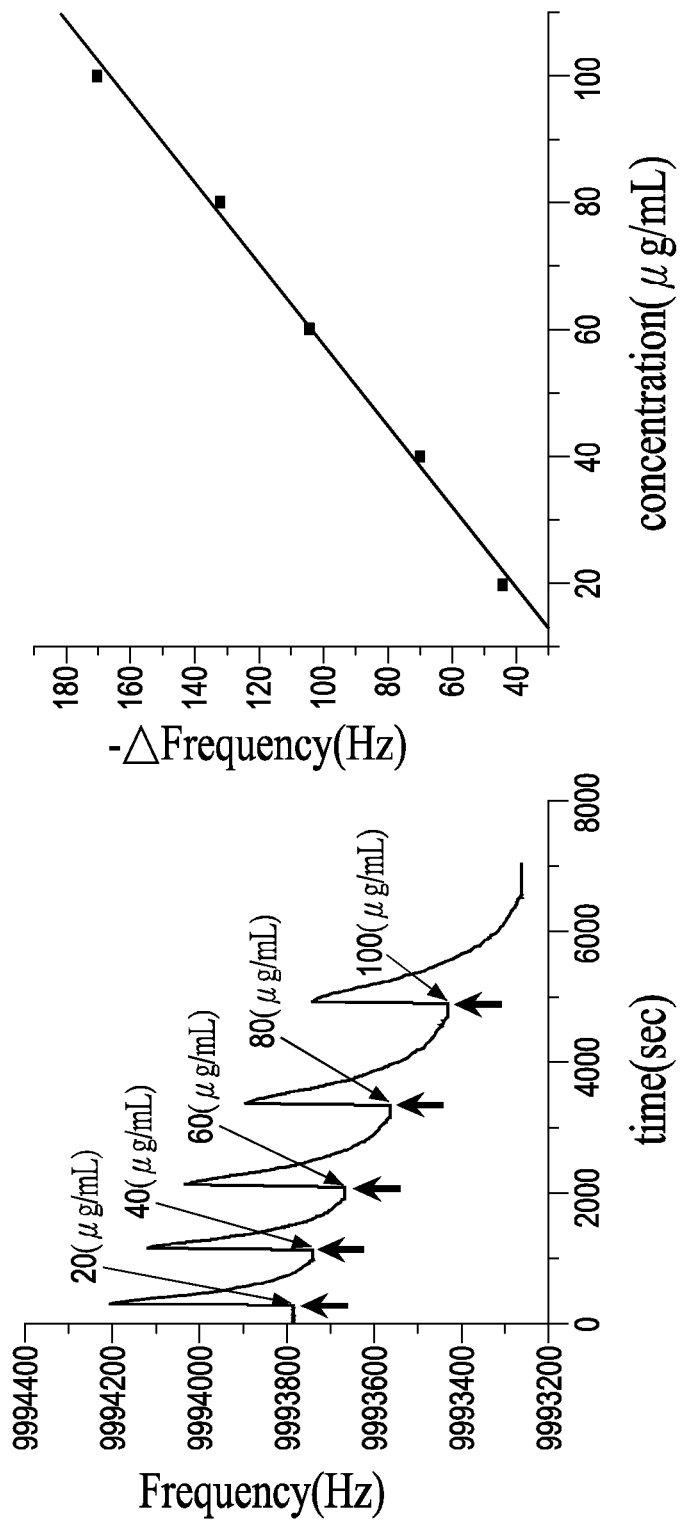
FIG. 7B shows the change of frequency of the biochip reacting with various concentrations of streptavidin with USW excitation at 300 kHz.

As FIG. 7B shows, the USW excitation has been used as the experimental method described in "The sensitivity of the biochip with USW excitation", and the corresponding frequency shifts from 43 to 166 Hz with a good linear relation with correlation coefficients of 0.998, standard deviations of 3.48 Hz and a slope of 1.57 Hz/(μg/mL). A sensitivity of the biochip for the USW excitation with the frequency of 185 kHz is 1.57 Hz/(μg/mL), smaller than the sensitivity of the biochip for the USW excitation with the frequency of 185 kHz, which is 2.33 Hz/(μg/mL). The result elucidates two points: 1) temperature rise due to the piezoelectric element actuation to produce ultrasonic waves is not a major factor to enhance sensitivity of the biochip. 2) Acoustic radiation force resulting from the USW excitation to maneuver bio-particles towards the sensing surface dominates the sensing enhancement mechanism.

To sum up, the present invention provides a brand new biochip with a piezoelectric element which can generate a USW to improve the sensitivity of the biochip, and a biotin-streptavidin binding model is used in experiments with the biochip. It is seen that immobilization of biotin during initialization of the biochip is enhanced by the USW excitation during the experiments, and the USW excitation provides improved biochip sensitivity and reduces the required time to reach equilibrium. All positive effects of the results mentioned above come from the USW excitation, and are unrelated to temperature effects. The present invention is useful for incorporation into practical commercial systems for enhanced real-time in-situ detection in medical and pharmaceutical applications.

What is claimed is:

1. A biochip with a piezoelectric element for ultrasonic standing wave generation, comprising an upper module, a lower module and a chemical sensor;
   the upper module having a carrier, a photoresist layer, a flow inlet, a flow outlet, an opening of a reaction chamber, a piezoelectric element, an O-ring and multiple spacers, said photoresist layer formed on one of two surfaces of said carrier; the flow inlet, the flow outlet and the opening of the reaction chamber formed through the photoresist layer and the carrier; the piezoelectric element set on a surface of the photoresist layer; the O-ring set on the other surface of said carrier surrounding the opening of the reaction chamber and the spacers set on the other surface of the carrier near edges;

the lower module having a carrier, an O-ring and multiple spacers, the carrier, the O-ring and the spacers of the lower module set corresponding to the carrier, the O-ring and the spacers of the upper module, respectively; and the chemical sensor mounted between the O-ring of the lower module and the O-ring of the upper module, attaching the upper module and the lower module such that the chemical sensor encloses the opening of the reaction chamber, wherein said photoresist layer is an epoxy-based negative coating with a viscosity of 51500 cSt, and a thickness of from 100 μm to 2 mm.

2. The biochip with a piezoelectric element for ultrasonic standing wave generation according to claim 1, wherein said chemical sensor is a quartz crystal microbalance sensor, a surface plasmon resonance sensor or a particle plasmon resonance sensor.

3. The biochip with a piezoelectric element for ultrasonic standing wave generation according to claim 2, wherein said piezoelectric element generates ultrasonic standing waves.

4. The biochip with a piezoelectric element for ultrasonic standing wave generation according to claim 3, wherein said piezoelectric element generates ultrasonic standing waves with a frequency from 100 kHz to 2 MHz.

5. The biochip with a piezoelectric element for ultrasonic standing wave generation according to claim 4, wherein said piezoelectric element generates ultrasonic standing waves with a frequency at 185 kHz.

6. The biochip with a piezoelectric element for ultrasonic standing wave generation according to claim 3, wherein a distance between said piezoelectric element and said chemical sensor is from 0.2 mm to 4 mm.

7. The biochip with a piezoelectric element for ultrasonic standing wave generation according to claim 6, further comprising a function generator and an amplifier, wherein said function generator produces a driving signal, the driving signal amplified by said amplifier and delivered to said piezoelectric element to generate ultrasonic standing waves.

8. The biochip with a piezoelectric element for ultrasonic standing wave generation according to claim 4, wherein a distance between said piezoelectric element and said chemical sensor is from 0.2 mm to 4 mm.

9. The biochip with a piezoelectric element for ultrasonic standing wave generation according to claim 4, further comprising a function generator and an amplifier, wherein said function generator produces a driving signal, the driving signal amplified by said amplifier and delivered to said piezoelectric element to generate ultrasonic standing waves.

10. The biochip with a piezoelectric element for ultrasonic standing wave generation according to claim 1, wherein said piezoelectric element generates ultrasonic standing waves.

11. The biochip with a piezoelectric element for ultrasonic standing wave generation according to claim 10, wherein said piezoelectric element generates ultrasonic standing waves with a frequency from 100 kHz to 2 MHz.

12. The biochip with a piezoelectric element for ultrasonic standing wave generation according to claim 11, wherein said piezoelectric element generates ultrasonic standing waves with a frequency at 185 kHz.

13. The biochip with a piezoelectric element for ultrasonic standing wave generation according to claim 10, wherein a distance between said piezoelectric element and said chemical sensor is from 0.2 mm to 4 mm.

14. The biochip with a piezoelectric element for ultrasonic standing wave generation according to claim 13, further comprising a function generator and an amplifier, wherein said function generator produces a driving signal, the driving signal amplified by said amplifier and delivered to said piezoelectric element to generate ultrasonic standing waves.

15. The biochip with a piezoelectric element for ultrasonic standing wave generation according to claim 11, wherein a distance between said piezoelectric element and said chemical sensor is from 0.2 mm to 4 mm.

16. The biochip with a piezoelectric element for ultrasonic standing wave generation according to claim 11, further comprising a function generator and an amplifier, wherein said function generator produces a driving signal, the driving signal amplified by said amplifier and delivered to said piezoelectric element to generate ultrasonic standing waves.

* * * * *